(12) United States Patent
Gleich

(10) Patent No.: US 9,603,544 B2
(45) Date of Patent: Mar. 28, 2017

(54) METHOD OF DETERMINING STATE VARIABLES AND CHANGES IN STATE VARIABLES

(75) Inventor: Bernhard Gleich, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 3340 days.

(21) Appl. No.: 10/552,806

(22) PCT Filed: Apr. 15, 2004

(86) PCT No.: PCT/IB2004/050449
§ 371 (c)(1),
(2), (4) Date: Oct. 11, 2005

(87) PCT Pub. No.: WO2004/091397
PCT Pub. Date: Oct. 28, 2004

(65) Prior Publication Data
US 2006/0210986 A1 Sep. 21, 2006

(30) Foreign Application Priority Data
Apr. 15, 2003 (EP) ..................................... 03101020

(51) Int. Cl.
| | | |
|---|---|---|
| G01N 19/00 | (2006.01) | |
| A61B 5/05 | (2006.01) | |
| G06F 19/00 | (2011.01) | |
| A61K 49/18 | (2006.01) | |
| B24B 49/00 | (2012.01) | |
| G06G 7/48 | (2006.01) | |

(52) U.S. Cl.
CPC .............. *A61B 5/05* (2013.01); *A61B 5/0515* (2013.01); *A61K 49/1887* (2013.01); *B24B 49/003* (2013.01); *G06F 19/30* (2013.01); *G06F 19/32* (2013.01)

(58) Field of Classification Search
CPC ................................. G06F 19/30; G06F 19/32
See application file for complete search history.

(56) References Cited

U.S. PATENT DOCUMENTS

| | | |
|---|---|---|
| 4,136,683 A | 1/1979 | Gordon |
| 4,267,234 A | 5/1981 | Rembaum |
| 4,452,773 A | 6/1984 | Molday |
| 4,537,861 A | 8/1985 | Elings |
| 4,554,088 A | 11/1985 | Whitehead et al. |
| 4,827,945 A | 5/1989 | Groman |
| 5,653,959 A | 8/1997 | Tournier |
| 6,082,366 A | 7/2000 | Andra et al. |
| 6,203,777 B1 | 3/2001 | Schroder |

(Continued)

FOREIGN PATENT DOCUMENTS

| | | |
|---|---|---|
| DE | 3751918 T2 | 3/1997 |
| DE | 10151778 A1 | 5/2003 |
| EP | 0095124 A1 | 5/1983 |
| EP | 1304542 A2 | 10/2002 |
| JP | 5340864 A | 12/1993 |
| WO | 9102811 A1 | 3/1991 |
| WO | 0235205 A2 | 5/2002 |

OTHER PUBLICATIONS

Heldemann et al. "A brief review of parallel magnetic resonance imaging" Eur Radiol (2003) vol. 13, pp. 2323-2337.*

(Continued)

*Primary Examiner* — Eric S Dejong

(57) ABSTRACT

The present invention relates to a method of determining physical, chemical and/or biological state variables, particularly substance concentrations, temperature, pH and/or physical fields, and/or the change in these state variables in an examination area of an examination object by determining the change in the spatial distribution of magnetic particles in this examination area as a function of the effect of influencing variables on at least a partarea and/or in the conditions in at least a part-area of the examination area, by means of the following steps: a) introducing magnetic particles into at least part of the examination area in a first state in which in the examination area or in parts thereof at least some of the magnetic particles that are to be examined are agglomerated and/or coupled to one another in pairs or more, or introducing magnetic particles into at least part of the examination area in a second state in which the particles are deagglomerated and/or decoupled and can be agglomerated and/or coupled, b) generating a magnetic field with a spatial profile of the magnetic field strength such that there is produced in the examination area a first part-area having a low magnetic field strength and a second part-area having a higher magnetic field strength, c) changing the, in particular relative, spatial position of the two part-areas in the examination area or changing the magnetic field strength in the first part-area so that the magnetization of the particles is locally changed, d) detecting signals that depend on the magnetization in the examination area that is influenced by this change, and e) evaluating the signals so as to obtain information about the change in the spatial distribution of the magnetic particles and/or about physical, chemical and/ or biological state variables or the change therein in the examination area. The invention further relates to magnetic particle compositions, in particular functionalized magnetic particle compositions and their use in a method according to the invention. The invention further also relates to an apparatus for the measurement of state variables in the examination area.

20 Claims, 2 Drawing Sheets

(56) References Cited

U.S. PATENT DOCUMENTS 6,216,540 B1 4/2001 Nelson
7,033,574 B1 4/2006 Schneider

OTHER PUBLICATIONS

Wasterby et al. "Anisotropic Water Diffusion in Macroscopically Oriented Lipid Bilayers Studied by Pulsed Magnetic Field Gradient NMR" Journal of Magnetic Resonance (2002) vol. 157, pp. 156-159.*
Zakharov et al. "Rotational viscocity, dynamic phenomena, and dielectric proerties in a long-chain liquid crystal" NMR Study and Theoretical Treatment (2000) Physical Review E, vol. 63, p. 011704-1 through p. 011704-8.*
Collin et al. "NR Characterization of a kissing complex formed between the TAR RNA element of HIV-I and a DNA aptamer", Nucleic acids research (2000), vol. 28, pp. 3386-3391.*
Piotto et al. "Gradient-Tailored excitation for single-quantum NMR specroscopy of aqueous solutions" Journal of Biomolecular NMR (1992), pp. 661-665.*
Evans "Biomolecular NMR Spectroscopy" Oxford Press. 1995, pp. 5-9, 11, 66, 71, 75, 76, and title page.*
J. M. Perez; "DNA-Based Magnetic Nanoparticle Assembly Acts as a Magnetic Relaxation Nanoswitch Allowing Screening of DNA-Cleaving Agents", MGH-Center for Molecular Imaging Research, Harvard Medical School, Dec. 14, 2001, vol. 124, No. 12.
W. S. Hinshaw; "Image Formation by Nuclear Magnetic Resonance: The Sensitive-Point Method", Dept. of Physics, Univ. of Pittsburg PA, vol. 47, No. 8, Aug. 1976.
Lee Josephson et al; "Magnetic Nonosensors for the Detection of Oligonucleotide Sequences", Angew. Chem. Int. Ed, 2001, vol. 40, No. 17.
Raymond Damadian et al; Tumor Imaging in a Live Animal by Field Focusing NMR (FONAR), Physiol. Chem. & Physics 8, 1976, pp. 61-65.
Shen, Lifen et al "Aqueous Magnetic Fluids Stabilized by Surfactant Bilayers", Journal of Magnetism and Magnetic Materials, vol. 19, 1999, pp. 37-44.
Kaiser, R. et al "Magnetic Properties of Stable Dispersions of Subdomain Magnetite Particles", Journal of Applied Physics, vol. 41, No. 3, 1970, pp. 1064-1072.
Menager, C. et al "Reversible Shrinkage of Giant Magnetoliposomes under an Osmotic Stress", Journal of Phys. Chemistry, vol. 106, 2002, pp. 7913-7918.

* cited by examiner

METHOD OF DETERMINING STATE VARIABLES AND CHANGES IN STATE VARIABLES

The present invention relates to a method of determining, particularly local, changes in state in an examination area by determining the spatial distribution and/or the change in the spatial distribution of magnetic particles in this examination area. The invention further relates to magnetic particle compositions, in particular functionalised magnetic particle compositions and their use in a method according to the invention. The invention further also relates to an apparatus for the measurement of state variables in the examination area.

For determining physical, chemical and biological state variables of any kind there are a large number of direct and indirect measurement methods available to the person skilled in the art, depending on the desired aim and the object that is to be examined. Often those measurement methods which can be used to determine state parameters in media which are not directly accessible to a measurement instrument or a measurement probe are of particular interest. Suitable examples of indirect parameter determination include the monitoring of reaction parameters such as temperature and the progress of the reaction in chemical preparation methods by means of optical methods or the determining of the quality of material parts, for example the existence of cracks, by means of ultrasound. Particularly when examining living tissue, it is often necessary to use indirect measurement methods to determine for example temperature, pH or the concentration of specific substances. However, such indirect measurement methods are often more complex and entail greater measurement errors than direct determination methods. Therefore, for many preparation methods or objects there is an increasing need for ways of being able to determine in a very precise manner the parameters that are to be examined, in a non-destructive and indirect manner. Those measurement methods which can be used to determine in a targeted manner information about locally closely delimited regions of an examination object are of particular significance.

One method for the non-invasive determination of chemical and physical states within an animal or human body can be found for example in EP 0 95 124 A. According to said document, the temperature and pH within selected volume segments in an examination area can be determined or found from the parameters of a measured nuclear resonance spectrum by using magnetic resonance spectroscopy with a homogeneous constant magnetic field and a high frequency magnetic field.

In one refinement of the method according to EP 0 95 124 A, besides a homogeneous constant magnetic field three orthogonally running gradient fields are generated which are modulated asynchronously in terms of time, as a result of which a local magnetic resonance signal is detected only at the intersection of the three planes of the gradient fields. This embodiment is described in the literature as the "sensitive point" method (cf. Hinshaw, J. Appl. Phys. 47 (1976), pages 3709 to 3721). According to EP 0 95 124 A it is furthermore possible to obtain information about the temperature and pH in living objects by superposing a gradient field on a homogeneous magnetic field such that only a narrowly delimited volume in the region of the measurement point that is to be examined has a high homogeneity and all surrounding regions have a considerably inhomogeneity. This method is known in the literature as the "FONAR" method (cf. Damadian, Physiol. Chem. Phys. 8 (1976), pages 61 to 65). One disadvantage of the measurement method proposed in EP 0 95 124 is that it is not readily possible to move the locally delimited examination area or allow it to migrate in order for example to be able to obtain reliable information about a larger coherent examination area or in order to be able to monitor at the same time local changes in the examination object. Although it has been possible in recent years to considerably increase the measurement speed by improving magnetic resonance imaging (MRI) methods, the determination of parameters such as temperature, pressure and pH is still too slow and inaccurate for many applications.

DE 37 51 918 T2 describes a method for obtaining an in vivo image of an animal or human organ or tissue with the aid of nuclear spin resonance technology, in which an image-improving dose of a nuclear spin tomography contrast agent is used in the form of a superparamagnetic fluid that is to be prepared in a specific manner. The magnetic properties of the examined tissue are said to be influenced by the magnetic contrast agent such that the irradiated protons exhibit an improved relaxation behavior. Superparamagnetic and ferromagnetic substances allow the magnetic resonance image to appear darker by reducing $T_2$. Suitable contrast agents for nuclear spin tomography nevertheless often require an extremely stable solution in order to be able to effectively increase the sensitivity of the nuclear resonance measurement. However, the stability of suitable aqueous fluids of superparamagnetic iron oxides is often considerably restricted by clumping together as a result of magnetic attraction forces between the particles. DE 37 51 918 T2 proposes a four-stage method for preparing a stable superparamagnetic fluid from divalent and trivalent metal salts. Although the magnetic particles obtained with this method may help to increase the anatomical and physiological contrast, they are often not suitable for making parameters such as temperature and pH more accurately and rapidly detectable using MRI technology. In addition, nuclear spin tomography requires the use of very strong magnetic fields having a high homogeneity. For this, use is usually made of supraconductive coils using cooling by means of liquid helium. The method of magnetic resonance tomography is consequently always associated with a high outlay on apparatus.

Nuclear spin resonance measurements, as described by Perez et al. (J. Am. Chem. Soc., 2002, 124 (12), pages 2856 and 2867), are likewise used to detect DNA interactions. Here, use is made of the fact that DNA or oligonucleotide sequences bound to magnetic particles hybridize with complementary DNA. If the complementary DNA is also bound to a magnetic particle, this may result in a stable cluster formation with the result that the $T_2$ relaxation times of water molecules adjacent to hydrogen nuclei decrease. This change can be made visible by means of nuclear spin tomography.

It is therefore an object of the present invention to make available a method of determining in particular locally delimited state variables in an examination area in a manner that is simple in terms of apparatus and hence cost-effective and also reproducible and accurate, which method also no longer has the disadvantages of the measurement methods of the prior art. Furthermore, it is an object of the present invention to provide a method for the locally delimited determination of physical, chemical or biological state variables or changes in state variables which can be used for the in situ determination of these state variables and allows the examination of materials and also of living matter.

Accordingly, there has been found a method of determining, particularly in situ, physical, chemical and/or biological properties or state variables, particularly substance concentrations, temperature, pH and/or physical fields, and/or the change in physical, chemical and/or biological properties or state variables in an examination area of an examination object by determining the change in the spatial distribution of magnetic particles in this examination area or in parts thereof as a function of the effect of, particularly physical, chemical and/or biological, influencing variables on at least a part-area and/or in the, particularly physical, chemical and/or biological, conditions in at least a part-area of the examination area, by means of the following steps:

a) introducing magnetic particles into at least part of the examination area in a first state in which in the examination area or in parts thereof at least some of the magnetic particles that are to be examined are agglomerated and/or coupled to one another in pairs or more, particularly covalently, ionically, coordinatively or via hydrogen bridge bonds or Van der Waals bonds, in particular are at least partially restricted in terms of their freedom of movement, or introducing magnetic particles into at least part of the examination area in a second state in which the particles are deagglomerated and/or decoupled and can be agglomerated and/or coupled, b) generating a magnetic field with a spatial profile of the magnetic field strength such that there is produced in the examination area a first part-area having a low magnetic field strength and a second part-area having a higher magnetic field strength, c) changing the, in particular relative, spatial position of the two part-areas in the examination area or changing the magnetic field strength in the first part-area so that the magnetization of the particles is locally changed, d) detecting signals that depend on the magnetization in the examination area that is influenced by this change, and e) evaluating the signals so as to obtain information about the change in the spatial distribution of the magnetic particles and/or about physical, chemical and/or biological state variables or the change therein in the examination area.

The method according to the invention makes use of the effect that magnetic particles change their properties when they are very close together. The magnetic particles that are close together are under the influence of each other's magnetic fields. Because of this, the response of the individual particles to external magnetic fields is changed due to the coupling with the magnetic fields of the neighbouring particles. By modifying the surroundings of the particles, a change in the distance between the particles and/or a change in the freedom of movement of these particles can be brought about in a targeted manner. The change in distance and the concomitant change in magnetic properties result in a different response to the applied external magnetic field in the magnetic particle imaging method. The different response is used to produce a contrast in the image. Preferably, the distance between the particles is less than 10 times, preferably less than 8 and more preferably less than 5 times the average diameter of the magnetic particles. With distance the core to core distance is meant. The closer the particles are, the stronger the mutual magnetic interaction and the higher the change in magnetic properties for a given change in distance. At a distance or than 10 times the average diameter the interaction becomes relatively weak and a change in distance does not result in a large change in magnetic properties. Similarly, if the magnetic particles are very close or even clumped together the change in distance does not result in a significant change in magnetic properties for the purpose of imaging. Further, it is very difficult to move the particles from each other when they are too close. In view that, the distance preferably is at least 2 times, preferably at least 3 times and more preferably at least four times the average particle diameter.

The method according to the invention makes substantial use of an arrangement as described in the unpublished German patent application having the number 101 51 778.5. Reference is hereby also made to the aforementioned patent application in respect of preferred embodiments of this arrangement.

A spatially inhomogeneous magnetic field is generated in the examination area by means of the arrangement used according to the invention. In the first part-area the magnetic field is so weak that the magnetization of the particles differs to a greater or lesser extent from the external magnetic field, that is to say is not saturated. This first part-area is preferably a spatially coherent area; it may also be a punctiform area or else a line or a flat area. In the second part-area (i.e. in the rest of the examination area outside the first part) the magnetic field is strong enough to keep the particles in a state of saturation. The magnetization is saturated when the magnetization of virtually all particles is aligned in approximately the direction of the external magnetic field, so that the magnetization there increases much less with a further increase in the magnetic field than in the first part-area given a corresponding increase in the magnetic field.

By changing the position of the two part-areas within the examination area, the (overall) magnetization in the examination area changes. If, therefore, the magnetization in the examination area or physical parameters influenced thereby is/are measured, information about the spatial distribution of the magnetic particles in the examination area can then be derived therefrom.

In order to change the spatial position of the two part-areas in the examination area or to change the magnetic field strength in the first part area, for example, a magnetic field that can be changed locally and/or temporally can be generated. It may also be provided that the signals induced in at least one coil by the temporal change in the magnetization in the examination area are received and evaluated in order to obtain information about the spatial distribution of the magnetic particles in the examination area. Signals that are as great as possible can be obtained by the spatial position of the two part-areas changing as rapidly as possible. A coil which is used to generate a magnetic field in the examination area can be used to detect the signals. However, at least one special coil is preferably used.

If the change in the spatial position of the part-areas takes place, for example, by means of a magnetic field that can be changed temporally, a likewise periodic signal is induced in a coil. However, this signal may be difficult to receive since the signals generated in the examination area and the temporally changing magnetic field are active at the same time; it is therefore not readily possible to distinguish between the signals induced by the magnetic field and the signals induced by changing the magnetization in the examination area. However, this can be avoided by a temporally changing magnetic field acting on the examination area in a first frequency band and, from the signal received in the coil, a second frequency band which contains higher frequency components than the first frequency band being evaluated so as to obtain information about the spatial distribution of the magnetic particles. This makes use of the fact that the frequency components of the second frequency band can occur only by virtue of a change in the magnetization in the examination area as a result of the non-linearity of the magnetization characteristic. If the temporally changing magnetic field has a sinusoidal periodic profile, the first frequency band consists only of a single frequency component—the sinusoidal fundamental component. By contrast, besides this fundamental component the second frequency band also contains higher harmonics (so-called upper harmonics) of the sinusoidal fundamental component, which can be used for the evaluation.

One preferred arrangement for the method according to the invention is characterized in that the means for generating the magnetic field comprise a gradient coil arrangement for generating a magnetic gradient field which in the first part-area of the examination area reverses its direction and has a zero crossing. This magnetic field is—if the gradient coil arrangement comprises e.g. two identical windings which are arranged on either side of the examination area but which are flowed through by opposite currents (Maxwell coil)—zero at a point on the winding axis and increases virtually linearly on either side of this point with opposite polarity. Only in the case of particles which are located in the region around this field zero point is the magnetization not saturated. In respect of particles outside this area the magnetization is in a state of saturation.

An arrangement may be provided with means for generating a temporally changing magnetic field that is superposed on the magnetic gradient field for the purpose of moving the two part-areas in the examination area. The area generated by the gradient coil arrangement is in this case moved around the field zero point, i.e. the first part-area, within the examination area by the temporally changing magnetic field. Given a suitable temporal profile and orientation of this magnetic field it is possible in this way for the field zero point to pass through the entire examination area.

The change in magnetization that is associated with the movement of the field zero point may be received by means of an appropriate coil arrangement. The coil used to receive the signals generated in the examination area may be a coil which is already used to generate the magnetic field in the examination area. However, there are also advantages to using a special coil for receiving, since this can be decoupled from the coil arrangement that generates a temporally changing magnetic field. Moreover, an improved signal-to-noise ratio can be achieved with one coil—but all the more so with a number of coils.

The amplitude of the signals induced in the coil arrangement is greater the quicker the position of the field zero point in the examination area changes, that is to say the quicker the temporally changing magnetic field superposed on the magnetic gradient field changes. However, it is technically difficult to generate on the one hand a temporally changing magnetic field whose amplitude is sufficient to move the field zero point to the point of the examination area and whose rate of change is sufficiently high to generate signals having a sufficient amplitude. Particularly suitable for this are those arrangements which have means for generating a first and at least a second magnetic field that are superposed on the magnetic gradient field, where the first magnetic field changes slowly in time terms and with a high amplitude and the second magnetic field changes rapidly in time terms and with a low amplitude. Two magnetic fields which change at different rates and with different amplitudes are generated—preferably by two coil arrangements. A further advantage is that the field changes may be so fast (e.g. >20 kHz) that they are above the limit of human audibility. It may likewise be provided that the two magnetic fields run essentially perpendicular to one another in the examination area. This allows the movement of the field-free point in a two-dimensional area. An expansion to a three-dimensional area is obtained by virtue of a further magnetic field which has a component that runs perpendicular to the two magnetic fields. An arrangement having a filter connected downstream of the coil arrangement is likewise advantageous, said filter suppressing from the signal induced in the coil arrangement the signal components in a first frequency band and allowing through the signal components in a second frequency band which contains higher frequency components than the first frequency component. This makes use of the fact that the magnetization characteristic in the region in which the magnetization passes from the unsaturated state to the saturated state is non-linear. This non-linearity means that a magnetic field which runs for example in a sinusoidal manner over time with the frequency f in the range of non-linearity brings about a temporally changing induction with the frequency f (fundamental component) and integer multiples of the frequency f (upper or higher harmonics). The evaluation of the upper harmonics has the advantage that the fundamental component of the magnetic field that is active at the same time for moving the field-free point does not have any influence on the evaluation.

According to one embodiment of the method according to the invention it is provided that those state variables in which magnetic particles pass from the first state to the second state are detected in an examination area, in particular by the relative arrangement of the magnetic particles changing toward a deagglomeration and/or decoupling and/or by the individual magnetic particles assuming on average a greater distance from one another, or in which the magnetic particles pass from said second state to said first state.

One refinement of the method according to the invention is further characterized in that the passing of the magnetic particles from the first state to the second state and/or from the second state to the first state takes place thermally, by means of radiation, acid, base, electrical or magnetic fields, ultrasound and/or enzymatically. By way of example, in the manner described above, initially free particles may form a covalent bond with one another if these particles are provided for example with suitable coatings which can react with one another.

Particularly if magnetic particles are linked via covalent or coordinative bonds, the method according to the invention can be used to examine states or changes in states in an examination object, e.g. in animal or human tissue, in which there is a break in the bond, as a result of which the relative spatial position of the previously bound particles with respect to one another changes in the examination area. If, for example, it is known at which pH an ester or amide bond is cleaved in a spacer molecule binding two magnetic particles, the examination area can be directly deduced therefrom. The relative change in the position of the magnetic particles with respect to one another on account of physical, chemical or biological influencing variables in the examination area can be made known by means of the method described above.

Accordingly, it has been found that the change in the spatial distribution of the magnetic particles that is determined in the examination area can be correlated with a local concentration, pressure, shear, viscosity, temperature and/or a local pH value. The method according to the invention is accordingly suitable for ascertaining the effect of substance concentrations, temperature, pressure, shear, pH and physical fields on the relative position or change in relative position of the magnetic particles with respect to one another and for determining the position thereof and/or the change in position thereof by means of the described imaging method.

It can also be ascertained if magnetic particles are pulverized or comminuted on account of, for example, shear.

According to a further aspect of the method according to the invention, it is provided that according to a first state agglomerated and or coupled-together magnetic particles are spatially delimited by a bond or liquid, solid or viscous medium which can be physically, chemically and/or biologically modified, dissolved and/or degraded. On account of the dissolving of the entire shell by external influences, the particles obtain a greater freedom of movement and can move away from one another, something which can be detected if the particles are in the first part-area of the gradient field.

As an alternative or in addition to the possibility of fixing magnetic particles to one another at a mutual distance via covalent bonds, the possibility is likewise provided of immobilizing magnetic particles in a suitable medium such that they are spaced as close together as possible. By introducing a number of such spatially restricted agglomerations of magnetic particles into an examination area, a very inhomogeneous particle distribution is firstly produced. By manipulating the medium in which the particles are embedded, for example by dissolving it, degrading it or allowing it to swell or gain volume, the magnetic particles are no longer restricted in terms of their freedom of movement and, depending on the conditions in the examination area, can distribute in the latter or move freely therein. This reduces the influence of one particle to an other.

It may be provided that the medium comprises polysaccharides, starch, in particular dextrins or cyclodextrins, waxes, oils, fats or gels.

According to a further refinement of the invention it is likewise possible that the medium comprises microorganisms, in particular bacteria.

By introducing magnetic particles into bacteria or parasites, e.g. plasmoids, it can be monitored for example at the same time when and under which conditions a bacterium is dissolved in a tissue, resulting in it being possible for the magnetic particles to escape from the bacterium.

In a further refinement of the method according to the invention it is provided that the magnetic particles in the agglomerated or coupled-together state are located in the region of the surface of a particulate, in particular liquid or gaseous, medium.

Since the magnetic particles are restricted for example to the border region or interface of a droplet of liquid or gel, it is possible to ascertain in a simple manner when and under which conditions a decrease or increase in size of the droplet volume takes place. By way of example it is possible in this way to monitor body fluids such as blood but also the progress of chemical methods, in particular in situ.

There is then accordingly a method of determining a, particularly local, change in state in an examination area of an examination object by determining the spatial distribution of magnetic particles in this examination area, where magnetic particles in a first state are agglomerated and/or releasably coupled to one another in a locally delimited medium, and on account of local conditions in the examination area or of the change in the conditions in this examination area are passed into a second state in which the magnetic particles are at least partially deagglomerated and/or separated or decoupled from one another. In this second state the magnetic particles on average are at a greater distance apart.

According to the invention it is provided that the magnetic particles become saturated upon application of an external magnetic field, in particular having a strength of about 100 mT or less. Of course, greater saturation field strengths are also suitable for the method according to the invention.

For many applications, suitable magnetic field strengths are even about 10 mT or less. This strength is sufficient even for many tissue or organ examinations. However, good measurement results can also be achieved with field strengths in the region of 1 mT or less or of around 0.1 mT or less. By way of example, concentration, temperature, pressure or pH can be determined with a high degree of accuracy and definition at magnetic field strengths of around 10 mT or less, of around 1 mT or less and at around 0.1 mT or less.

Within the context of the present invention, the term external magnetic field in which the magnetic particles become saturated or are saturated is to be understood as meaning a magnetic field in which around half the saturation magnetization is achieved.

Suitable magnetic particles are those which can become saturated in the case of a sufficiently small magnetic field. A necessary prerequisite for this is that the magnetic particles have a minimum size or a minimum dipole moment. Within the context of the present invention, the term magnetic particles also refers to magnetizable particles.

Suitable magnetic particles advantageously have dimensions which are small compared to the size of the voxels, the magnetization of which is to be determined by means of the method according to the invention. Furthermore, the magnetization of the particles should preferably become saturated at field strengths of the magnetic field which are as low as possible. The lower the field strength necessary for this, the higher the spatial resolution capability and the weaker the (external) magnetic field that is to be generated in the examination area. Moreover, the magnetic particles should have a dipole moment that is as high as possible and a high saturation induction in order that the change in magnetization results in output signals that are as great as possible. When using the method for medical examinations, it is also important that the particles are non-toxic.

According to a preferred refinement of the method according to the invention, it is proposed that the magnetic particle is a monodomain particle the magnetization of which can be reversed by means of Neel's rotation and/or by means of Brown's rotation.

Suitable magnetic monodomain particles are preferably dimensioned such that only a single magnetic domain (the monodomain) can form therein and there are no white regions. According to a particularly preferred variant of the invention, suitable particle sizes lie in the range from 20 nm to around 800 nm, with the upper limit also depending on the material used. In respect of monodomain particles, use is preferably made of magnetite ($Fe_3O_4$), maghemite ($\gamma$-$Fe_2O_3$) and/or non-stoichiometric magnetic iron oxides.

In general, it is advantageous, particularly when a rapid magnetization reversal by means of Neel's rotation is desired, that the monodomain particles have a low effective anisotropy. The term effective anisotropy is in this case to be understood as meaning the anisotropy resulting from the form anisotropy and the mean crystal anisotropy. In the aforementioned case, a change in the magnetization direction does not require any rotation of the particles. Alternatively, monodomain particles having a high effective anisotropy may also be used if it is desired that the magnetization reversal upon application of an external magnetic field is to take place by means of Brown's rotation or geometric rotation. Those particles the magnetization reversal of which is based on both Neel's rotation and Brown's rotation are especially suitable for viscosity measurements in particular.

According to an alternative embodiment of the method according to the invention it may be provided that the magnetic particle is a hard- or soft-magnetic multidomain particle. These multidomain particles are usually relatively large magnetic particles in which it is possible for a number of magnetic domains to form. Such multidomain particles advantageously have a low saturation induction.

Hard-magnetic multidomain particles essentially have the same magnetic properties as monodomain particles having a high effective anisotropy. Soft-magnetic multidomain particles with a low saturation magnetization have the advantage that they may be shaped in any way in order to be able to be used in the method according to the invention. If they have an asymmetric external shape, they are also particularly suitable for local viscosity measurements in the examination area. Soft-magnetic multidomain particles with a high saturation magnetization are advantageously to be configured such that the demagnetization factor is small. Both symmetric and asymmetric shapes can be used. For example, a soft-magnetic active substance with a high saturation magnetization may be applied as a thin coating to a sphere or a cube which itself cannot be magnetized. Soft-magnetic multidomain particles with a high saturation magnetization which have an asymmetric shape, e.g. in the form of disks or needles, may again be used for viscosity measurements.

Accordingly, monodomain particles the magnetization of which is reversed by means of Neel's and Browns' rotation and soft-magnetic multidomain particles with a low or high saturation magnetization which have an asymmetric external shape are particularly suitable for local viscosity measurements in the examination area.

As already mentioned, the magnetic particles likewise comprise those particles having a non-magnetic nucleus and a coating consisting of a magnetic material. Furthermore, in principle those magnetic particles which have a low effective anisotropy and also those which have a high effective anisotropy can thus be used. In the case of semi-hard magnets and in particular hard magnets, a high coercive force Hc is often required to bring the magnetization to zero. Suitable hard-magnetic materials comprise Al—Ni, Al—Ni—Co and Fe—Co—V alloys and also barium ferrite (BaO 6xFe$_2$O$_3$).

According to a further aspect of the method according to the invention, it is provided that first magnetic particles, bound to at least one functional binding unit, in particular a functional group, a DNA sequence, an RNA sequence and/or an aptamer, and at least second magnetic particles, bound to at least one functional binding unit, in particular a functional group, a DNA sequence, an RNA sequence and/or an aptamer, are present in and/or introduced into the examination area and that there is present in and/or is introduced into the examination area at least one compound which has at least a first functional binding unit, in particular a functional group, a complementary DNA sequence, a complementary RNA sequence and/or a complementary aptamer sequence, that interacts in a binding manner with at least one functional binding unit of the first magnetic particles and which has at least a second functional binding unit, in particular a functional group, a complementary DNA sequence, a complementary RNA sequence and/or a complementary aptamer sequence, that interacts in a binding manner with at least one functional binding unit of the second magnetic particles.

In this way it is possible for example to ascertain, in an examination area or examination solution, whether there is a target molecule which has for example two or more specific binding points for different functional binding units that are directly or indirectly bound to the first and second magnetic particles, and at which concentration this target molecule is present. Thus, for example, a first magnetic particle having a DNA sequence A and a further, second magnetic particle having a DNA sequence B may be bound. If there is also in the examination area or examination solution a target molecule which has both an oligonucleotide strand that is complementary to sequence A and an oligonucleotide strand that is complementary to sequence B, the two previously described first and second magnetic particles can be fixed to the target molecule at a slight distance apart. In this way the detectable magnetization reversal behavior which can be observed according to the method outlined above changes for the examination area. In this way it can be very rapidly and efficiently determined whether and which binding partners are present in an examination area or examination solution.

If on the other hand the initial state is one in which first and second magnetic particles are present on a common target molecule via identical or different binding units, then when these bonds are cleaved, e.g. by the presence of suitable enzymes such as DNAses, the spatial change in the magnetic particles can likewise be detected by way of a changed magnetization reversal behavior.

Oligonucleotide sequences and DNA bound to magnetic particles are described for example by Perez et al. (J. Am. Chem. Soc., 2002, 124 (12), pages 2856 and 2867) and by Josephson et al. (Angew. Chem., Int. Ed. 2001, 40 (17), pages 3204 to 3206).

Magnetic particles can also be coupled to one another for example by the surfaces of these particles being completely or partially functionalized, for example silanized, and a bond between the thus functionalized surfaces of the particles being produced via one or more spacer molecules. The preparation of silanized magnetic oxide particles is described for example in U.S. Pat. No. 4,554,088. Silanized paramagnetic iron oxide particles are commercially available for example as BioMag 4100 from Paesel & Lorei, Frankfurt. These magnetic particles have a diameter of between 0.5 and 1.5 μm and comprise primary amino groups as functional units. Furthermore, magnetic particles can be activated with tosyl chloride.

According to a further embodiment, the magnetic particles may be provided with a polymer coating, for example with a polyglutaraldehyde shell, as described in U.S. Pat. No. 4,267,234, or with a dextran coating, as disclosed in U.S. Pat. No. 4,452,773. Furthermore, the magnetic particles may likewise be provided with a coating of polysaccharides, a protein and/or a polypeptide. These coatings may be covalently coupled to one another in a further step either directly or again via at least one spacer molecule in a manner known to the person skilled in the art. Of course, it is also possible for the magnetic particles to be provided with a plastic coating, for example a layer of a polystyrene latex or of polyacrylamide, in order for a coupling then to take place. The type of coupling reaction selected essentially depends on the functional groups on the surface of the coating of the magnetic particle and the functional groups of the spacer molecule. Suitable coupling reactions may be induced radically, thermally, under acidic or basic conditions or by means of radiation. The coating of the magnetic particles with organic polymers for example additionally has the advantageous effect that the magnetic particles do not tend to clump together on account of magnetic attraction, neither in the agglomerated or coupled-together state nor in the state of free movement.

Suitable agglomerates of coated and uncoated magnetic particles can be produced for example by introducing a number of such magnetic particles into a solid or viscous shell, for example into spheres or drops of wax, oil or fat. Furthermore, agglomerates may be obtained by incorporating or embedding a number of magnetic particles in gels, e.g. agar gels, in particular swellable gels, or glycerin for example.

Using the method according to the invention it is possible for example for local temperature, pH and/or concentration values or changes therein to be determined by an image of the distribution of the magnetic particles in the examination area being created before a change in the particle distribution in the examination area takes place.

By way of example, in the case of particle agglomerates present in gel or wax droplets, a saturation magnetization occurs only at relatively high field strengths, resulting in a poorer resolution or lack of definition in the image obtained. If the agglomerates dissolve, e.g. on account of a change in the temperature and/or pH, and if the distance between the particles increases, the magnetization curve assumes a steeper profile and the saturation magnetization is achieved even at a relatively low field strength, allowing a higher resolution to be obtained. By comparing changing particle distributions with a previously determined particle distribution, for example one determined in the basic state, then the conditions under which a change of state takes place in the examination area and the extent thereof can readily be deduced.

Furthermore, according to a second effect a change in the distance between magnetic particles in an examination area can also be made visible with the aid of the method according to the invention by virtue of the fact that individual, i.e. free magnetic particles behave isotropically in a magnetic field whereas an anisotropic behavior can be seen in respect of two or more agglomerated magnetic particles or magnetic particles coupled to one another via spacer molecules. In this case, the procedure may be for example that a strong, substantially homogeneous magnetic field is applied in one direction and then there is a wait until all magnetic particles are aligned. This state is determined using the method according to the invention, with a very short measurement interval preferably being selected in order not to change the order too much. This examination process is repeated, but with a changed orientation of the measurement magnetic field, in order to be able to deduce an anisotropic behavior from the difference in the measurement data obtained. Since it is possible to precisely determine the location at which the anisotropy occurs using the method according to the invention, and in addition it is also readily possible to determine under which external conditions this change in state or anisotropy has occurred, it is possible for useful information to be determined, e.g. in terms of measured local temperature, pH and/or concentration parameters, in a small, clearly defined examination area.

Furthermore, as an alternative or in addition, a further, third contribution to the local determination of parameters in the examination area can be used when the examination area is examined using the method according to the invention, i.e. is scanned with the field-free point. For instance in the case of small examination objects, in the presence of a hysteresis, the response signal of the field-free point may be obtained in a time-delayed manner, and this is made visible by a relative shift in the image obtained. Since magnetic particles that are coupled to one another or agglomerated have an effect on the area enclosed by the magnetization curve, at a given measurement frequency it is possible to draw conclusions about the coupling or agglomeration of magnetic particles. The hysteresis behavior mentioned above usually then has no influence on the data determined if all the magnetic particles are very small, since in this case the influence of thermal energy is predominant.

In order that accurate and reliable data can be obtained by means of the phenomena described above, it has proven advantageous to include upstream at least one calibration measurement. For this, the measurement is taken at a sufficiently large number of locations in the case of a sufficiently large number of external influences which change the magnetic particles, in a predefined sequence. This sequence must be configured such that the received signal changes to a sufficiently great extent from location to location and in the case of different external parameters. Points and values which have not been measured by calibration are obtained by suitable interpolation. In this way a set of basic functions is obtained. The signal measured in the object or examination area is developed according to these basic functions. The development coefficients can be combined to form various images, in each case for different external parameters. The intensity at a given location in the examination area in these images may in this case be used as a measure of the external parameter at this location.

Accordingly, according to a further aspect of the present invention there is provided an evaluation method, essentially comprising the following steps:

a) selection of a path for the movement of the first part-area having a low magnetic field strength within the examination area, b) recording of reference data by means of reference samples along the path according to a) at at least one location, in particular a number of locations, in the case of at least two, in particular a number of, external parameters using at least a first receiving coil, c) interpolation and/or extrapolation of the reference data recorded in b) in respect of points and external parameters not recorded in step b), d) measurement of the path within the examination area in a sequence that is identical or substantially identical to that used for the recording of data by means of reference samples according to b) via at least a first and/or second receiving coil, and e) comparison of the data obtained according to d) with the reference data according to b) and/or c), in particular by means of error square minimization.

In a further embodiment, in a step c') that follows step c), the reference data obtained in steps b) and/or c) are converted to the characteristics of at least a second receiving coil used for the measurement in step d).

According to the invention it may furthermore be provided that in a further step f) the data obtained by means of comparison in step e) are assigned to a gray value for a pixel to give an image, with the relative pixel intensity representing the degree of the determined external parameters.

According to the invention it may furthermore be provided that in a further step g) the images obtained in step f) are displayed in a merged image. In this case, for example the brightness may provide information about the resolution and the color selected may provide information about a parameter such as temperature, concentration or pH in the examination area.

In a particularly preferred embodiment, the method according to the invention is characterized in that steps c') to g) or d) to g) are carried out at least twice, in particular a number of times.

A suitable path for measuring properties in an examination area may be carried out, for example, such that the part-area having a low magnetic field strength is moved by actuating and/or moving the coil arrangement. Furthermore, it is possible that in the case of a stationary part-area having a low magnetic field strength the examination object is moved in the desired manner. Simultaneous movement of examination object and part-area having a low magnetic field strength are also possible.

A path is defined by the spatial change in the weak-field or field-free part-area of the gradient field through an examination area. It is consequently a so-called zero point path. A suitable path may be prescribed for example by two alternating magnetic fields having a different direction but the same frequency and may describe a circle. Alternatively, the ratio of the frequencies of these fields may be an integer multiple and lead to folded structures. A particularly dense sampling and hence also referencing of the examination area is achieved when the (zero point) path describes a Lissajous figure. The reference data determined at the respective positions in the examination area are determined in the case of at least two known external parameters, e.g. different temperatures or pH values, in the examination area and used for referencing. The reference sample characterizes a region in the examination area the magnetic state of which (e.g. particle type, concentration and distribution) is known. The referencing or calibration may be carried out both on the actual examination object and on an (in vitro) reference sample as long as the measurement conditions in the examination area can be reliably adjusted.

The recording of reference data may be omitted if the properties or the behavior of the magnetic particles in a referenced examination area are already sufficiently well known and all the necessary reference data can be calculated from a single recording of the magnetic behavior of the examination area.

The recording of reference data may be omitted if the properties of the contrast agent in the case of the possible parameters of the examination area are sufficiently accurately known. In this way the necessary reference data may already be calculated. Only via the detection of the change in the magnetization behavior can conclusions then be drawn about physical, mechanical, chemical or biological states or changes in state in the examination area.

The method according to the invention is suitable for controlling or determining changes in state in solid, liquid, viscous and gaseous examination areas or media. These examination areas and media may be present in living or dead tissue or organs or in living or dead organisms, for example microorganisms, plants or humans. These examination areas or media may furthermore be present in organic or inorganic materials, for example plastics.

The invention also relates to magnetic particle compositions that can be used in the method according to the invention. The inventors found various embodiments of such magnetic particle compositions as will be described below.

One embodiment of a magnetic particle composition is a magnetic gas bubble composition, comprising one or more gas bubbles in a liquid medium wherein magnetic particles are present at the interface of the gas bubble and the liquid medium. The average particle to particle distance between the magnetic particles at the interface between the gas bubble and the liquid medium is preferably between three in 10 times the average diameter of the magnetic particles and is preferably less than 8, more preferably less than 5 times the magnetic particle size. The magnetic gas bubble composition may comprise a surfactant for localising the magnetic particles substantially at the interface between the gas bubble and the liquid medium. Preferably, the magnetic particles are attached to a surfactant molecule. The size of the magnetic gas bubble can in principle vary in a wide range. In a preferred use of the magnetic particle imaging method, for examining living organisms, the diameter of the gas bubble is preferably between one and 10 µmeters. Preferably, the magnetic gas bubble comprise a gas having a low water solubility, in particular wherein the gas does not substantially dissolve and/or does not rapidly dissolve in water. A suitable not dissolvable gas for in the body applications is a perfluorated gas.

Magnetic gas bubble composition is can be made in different ways. One way is to introduce gas bubbles in a liquid medium. A disadvantage of liquid magnetic gas bubble composition is that the storage stability is relatively low and they are relatively difficult to make. According to another aspect of the invention there is provided a magnetic gas bubble precursor for the manufacture of a magnetic gas bubble composition wherein the gas bubble precursor comprises a shell encompassing a gas volume and wherein the shell comprises magnetic particles. The magnetic dry gas bubble precursor can be used in the dry state, but are preferably used for the manufacture of a magnetic gas bubble composition as described above, for example by dissolving a dry magnetic gas bubble precursor in a suitable liquid medium. The advantage of this dry magnetic gas bubble precursor is that it can be stored with a relatively long shelflife.

The magnetic gas bubble precursor can be administered to the examination area directly in case the examination area contains a liquid medium. The magnetic gas bubble precursor can also be administered after dispersing in a liquid medium. The shell material may at least partly dissolve or reduce viscosity in contact with the liquid medium such that the magnetic particles gain freedom for rotational movement when dispersed in the liquid medium. The shell material can for example be a material that dissolves in an aqueous medium like blood, for example a polysaccharide, a starch or a low viscosity hydrophilic polymer material. The shell material can also be a material that melts or reduces viscosity at the temperature prevailing in the examination area or a material that degrades or decompose to a low viscosity in conditions prevailing in the examination area.

The dry gas bubble precursor can also be used as an aerosol.

The invention also relates to the use of a magnetic gas bubble composition or a magnetic gas bubble precursor according to the invention as an imaging agent in a magnetic particle imaging technique, in particular for imaging pressure in an examination area by said technique, more particular for imaging elastic properties of the examination area by acoustic waves.

The bubble may comprise a drug. The drug may be transported to a specific area in the examination fields in a controlled manner controlled by the imaging technique, and locally released by destroying the gas bubble, for example by using the magnetostriction effect or by irradiation was electromagnetic radiation or by accoustic waves.

The invention also relates to a kit of magnetic particle compositions for use in the method according to the invention described above, comprising a first magnetic particle composition, a second magnetic particle composition and a third compound, wherein in the first magnetic particle composition the first magnetic particles are bound to at least one functional binding unit, in particular a functional group, a DNA sequence, an RNA sequence and/or an aptamer, wherein in the second particle composition the second magnetic particles are bound to at least one functional binding unit, in particular a functional group, a DNA sequence, an RNA sequence and/or an aptamer and wherein the third compound is has at least a first functional binding unit, in particular a functional group, a complementary DNA sequence, a complementary RNA sequence and/or a complementary aptamer sequence, that interacts in a binding manner with at least one functional binding unit of the first magnetic particles and which has at least a second functional binding unit, in particular a functional group, a complementary DNA sequence, a complementary RNA sequence and/or a complementary aptamer sequence, that interacts in a binding manner with at least one functional binding unit of the second magnetic particles and wherein the average particle to particle distance in a state wherein the first and second magnetic particle bind with the third compound is such that the first and second magnetic particles are coupled in a first agglomerated state, preferably having a distance between the magnetic particles between 3 and 10 times the magnetic particle size.

According to the invention there is also provided a magnetic composition comprising two or more magnetic particles that are according to a first state agglomerated and/or coupled-together in a spatially delimited way by a bond and/or by embedding in a solid or viscous medium which bond and/or embedding medium can be physically, chemically and/or biologically modified, dissolved and/or degraded to a second state of reduced agglomeration and wherein the average particle to particle distance between the magnetic particles is less than 10 times the average magnetic particle size.

In a preferred embodiment of said magnetic composition the two or more magnetic particles are coated with a shell material that is does not quickly dissolve or degrade and are agglomerated and kept together with a bond that can be physically, chemically and/or biologically broken to a second state of reduced agglomeration. The advantage of this embodiment this that the shell of the magnetic particles prevents the particles from re-agglomerating or clumping after the bond is broken. Preferably, the diameter of the coated magnetic particle including the shell is at least two times the diameter of the magnetic particle.

The state or shape of the magnetic composition is broadly defined. It may for example be a paste coated on to a surface to detect changes in movement or physical or chemical state of a surface. For examination of living organisms, the magnetic composition preferably is in the shape of particles or an emulsion of particles. In the agglomerated first state the average particle to particle distance between the magnetic particles is preferably between 3 and 10 times the average magnetic particle size for reasons as described above.

A preferred embodiment of the invention concerns a functionalised magnetic particle composition comprising coated particles comprising two or more magnetic particles wherein the average particle to particle distance between the magnetic particles is between 3 and 10 times the magnetic particle size and which particles are in a first state agglomerated and/or coupled-together state and are coated with a spatially delimited, solid or viscous coating material which can be physically, chemically and/or biologically modified, dissolved and/or degraded. Preferably, the magnetic particles are coated with a coating material that swells or shrinks to an extent depending on the conditions in the examination area, thereby changing the distance between the magnetic particles. In this functionalised magnetic particle composition the extent of swelling of the coating material for example depends on and hence can be used to measure the ion strength of the aqueous medium in the examination area, in particular body fluids.

In general the magnetic particles in the magnetic particle composition, are chosen such that good magnetic particle images, in particular a good resolution can be obtained in a given field gradient. In unpublished German patent application number 101 51778.5 a magnetic particle imaging method is described. It is generally described that magnetic mono-domain particles having a size between 20 and 800 nanometers or a glass beat coated with a magnetic coating can be used in this method. However, in order to achieve a good magnetic imaging contrast and resolution at relatively low magnetic field gradients, improved magnetic particle compositions are highly desirable. The inventors have found magnetic particles having improved magnetic particle imaging properties.

Preferably, the magnetic particles in the magnetic particle composition have a magnetization curve having a step change, the step change being characterized in that the magnetization change, as measured in an aqueous suspension, in a first field strength window of magnitude delta around the inflection point of said step change is at least a factor 3 higher than the magnetization change in the field strength windows of magnitude delta below or in the field strength windows of magnitude delta above the first field strength window, wherein delta is less than 2000 microtesla, preferably less than 1000 microtesla, and wherein the time in which the magnetisation step change is completed in the first delta window is less than 0.01 seconds, preferably less than 0.005 sec, more preferably less than 0.001, most preferably less than 0.0005 seconds. It has been found, that such magnetic particles are particularly suitable for magnetic particle imaging, in particular for obtaining a good resolution of the image. It is further preferred, that the magnetic particle composition has a magnetisation curve, wherein the step change is at least 10%, preferably at least 20%, more preferably at least 30% and most preferably at least 50% of the total magnetisation of the particle composition as measured at an external magnetisation field of 1 Tesla. It is further preferred, that the magnetization change in the first field strength window of magnitude delta around the inflection point of said step change is at least a factor 4, preferably at least a factor 5 higher than the magnetization change in the field strength windows of magnitude delta below or in the field strength windows of magnitude delta above the first field strength window.

The magnetic particle composition is particularly useful for use in a magnetic particle imaging technique. The particles show good spatial resolution at relatively low field strength gradients. Further, the magnetic particle composition allows for a relatively high scanning speed for examining a large examination area. For example, for application in medical magnetic particle imaging, where the step change occurs preferably at a delta value below 1000 microTesla, the particle composition has a resolution value better than between 0.1 and 10 mm at magnetic field strength gradients between 10 and 0.1 T/m. With the magnetic particle imaging technique using the magnetic particle compositions according to the invention extremely good resolution can be obtained, for example in a range from 0.1 to 10 micrometers in applications, where are very high magnetic field is gradients can be achieved, for example in microscopy.

It is preferred that the magnetic particle composition showing the required step change as described above is used in the method and all the magnetic particle compositions according to the invention.

It is noted that strictly speaking, magnetic field strength is expressed in H (A/m). However, in the present application, when reference is made to magnetic field strength, B-fields are meant. A magnetic fields B of 2000 µT as described above corresponds to an H field of 2 mT/$\mu_0$=1.6 kA/m, that is the equivalent H field that would produce a B field of 2 mT in vacuum.

A method for measuring the magnetisation curve and the required step change is as follows. A sample of a magnetic particle composition is suspended in water, optionally with the help of a simple detergent. To prevent clumping and/or to de-agglomerate the magnetic particles an ultrasound treatment possible can be used. The concentration of the magnetic particle composition is less than 0.01 gr core mass per liter of solvent. With core mass is meant the mass of the magnetic material in the magnetic particle composition. The suspension is brought into a fast magnetometer. (i.e. a device that measures the magnetization of the sample while an external field is applied). Suitable fast magnetometers are known to the expert. The magnetometer is equipped with means allowing to produce an external field at the sample position in at least two orthogonal directions simultaneously, i.e. to produce any magnetic field below a given maximum amplitude and a given maximum speed of change. The magnetisation is measured also in at least two orthogonal directions in the same plane.

First the saturation magnetisation is measured. For this, a magnetic field of about one Tesla is applied in one direction and the magnitude of magnetization is measured after at least 10 seconds. Then the measurement sequences for determining the step change starts. The sequence starts with choosing a field vector with an external field magnitude below 20 mT. This field is applied for at most 100 seconds. Then a second direction is chosen. This direction defines the scalar values of the field H and the magnetization M. The field is rapidly changed, preferably less than 1 millisecond, so that it lies now in −H direction with some magnitude below 20 mT. Then the field is changed from −H to +H e.g. in a linear way and the (now scalar i.e. projected) magnetization is recorded. The magnetization curve is recorded in less than 0.01 s but longer than 1 µs. Where the magnetisation curve shows a step change, a first window of size delta is positioned centrally on the inflection point of the magnetisation step change. Similarly, a window of size delta is positioned below and above the first window, and the required step change is evaluated by determining the change in magnetisation in each of the windows.

Whether or not a given magnetic particle composition has the required step change depends in a complicated way on many variables, for example of the size of the particles, the particle size distribution, the shape of the particles, the damping constant for Neel rotation, the type of magnetic material, the crystallinity and the stochiometry of the composition of the magnetic material. It has been found that it is particularly important that the particle size distribution of the particle composition is narrow. Preferably, the magnetic particle composition according to the invention has a narrow particle size distribution wherein at least 50 weight % of the particles have a particle size between plus or minus 50%, preferably 25%, more preferably 10% of the average particle size. Preferably, the amount of particles within the specified windows, is at least 70 wt %, preferably at least 80 wt %, and most preferably at least 90 wt %. Particularly good results are obtained with mono-domain particles have a low magnetic anisotropy with a field needed for inducing Neel rotation of substantially below 10 mT, preferably below 5 mT, more preferably below 2 mT. Preferably, the magnetic particles are mono-domain particles having an average particle size between 20 and 80 nanometers, more preferably between 25 and 70 nanometers, musst preferably between 30 and 60 nanometers, wherein at least 50, preferably at least 60, more preferably at least 70 weight % of the particles have a particle size between the average particle size plus or minus 10 nanometer.

In an alternative embodiment of the magnetic particle composition according to the invention, the magnetic particle is a multi-domain particle having substantially a needle shape having a demagnetisation factor of less than 0.001. This magnetic particle composition is particularly useful in non-medical applications where the needles shape is not a disadvantage. In another alternative embodiment, the magnetic particle composition according to the invention comprises magnetic particles comprising a non-magnetic core covered with a magnetic coating material, wherein the thickness of the coating is between 5 and 80 nanometers and wherein the demagnetisation factor is less than 0.01 and a diameter below 300 µm. Also in these alternative embodiments it is advantageous to have a small particle size distribution as described above. The physical parameters of the magnetic particles in these embodiments are preferably chosen to meet the step change requirement as described above for achieving good imaging properties.

The magnetic particle composition according to the invention can be manufactured by first forming magnetic particles, for example by precipitation, for example by contacting a solution comprising ferrous and ferric ions with a solution comprising sodium hydroxide as described above. In principle, a known precipitation process can be used. It is also possible to grind the particles from bulk material, for example using a high speed ball mill. The essential next step for obtaining a good magnetic particle composition is the selection and separation of the particles. The first step is to perform a size selection process by filtering and/or centrifuge methods. The next step is to perform a selection process based on the magnetic properties of the particles, for example, using oscillating magnetic gradient fields.

The invention also relates to an apparatus to determine the spatial distribution of magnetic particle and/or in situ, physical, chemical and/or biological properties or state variables, particularly substance concentrations, temperature, pH and/or physical fields, and/or the change in physical, chemical and/or biological properties or state variables in an examination area of an examination object comprising:

a) means to generate a magnetic field with a spatial distribution of the magnetic field strength such that the area of examination consists of a first sub-area with lower magnetic field strength and a second sub-area with a higher magnetic field strength, b) means to change the spatial location of both sub-areas in the area of examination so that the magnetization of the particles changes locally, c) means for the acquisition of signals that depend on the magnetization in the area of examination influenced by this change, d) means for the evaluation of said signals to obtain information about the spatial distribution of the signals in the area of examination and e) means to perform calibration measurements, preferably according to the calibration method as described above, comprising means to record reference data on reference samples and means to compare the signals obtained in step c and/or d with the reference data to evaluate spatially resolved information about in situ, physical, chemical and/or biological properties or state variables in the area of examination.

The present invention is based on the surprising knowledge that useful conclusions can be drawn about characteristic physical, chemical or biological properties or changes therein in an examination area only by the change in the distance of magnetic particles from one another in said examination area. By way of example it is possible to covalently bond two or more magnetic particles to one another via a spacer unit, with it being possible for this spacer to be cleaved in the presence of suitable enzymes, as a result of which the presence and concentration of specific enzymes in an examination area can be determined. The spacer may also have a characteristic ester or amide linkage which is cleaved only in the presence of specific enzymes. Likewise, magnetic particles may be covalently bonded to one another such that one or more functional groups which can be cleaved for example under acidic, basic or thermal conditions are integrated in the binding unit. In this way it is possible to separate the coupled magnetic particles in a locally delimited manner, as a result of which for example local temperature, pressure and pH values and instances of local particle shearing can be determined. One advantage of the present method is also that physical, chemical and biological information about the examination area or parts thereof can be obtained with a high spatial resolution. This relates to the examination of both biological and non-biological objects and phenomena.

The invention will be further described with reference to examples of embodiments shown in the drawings to which, however, the invention is not restricted.

Figure 1:
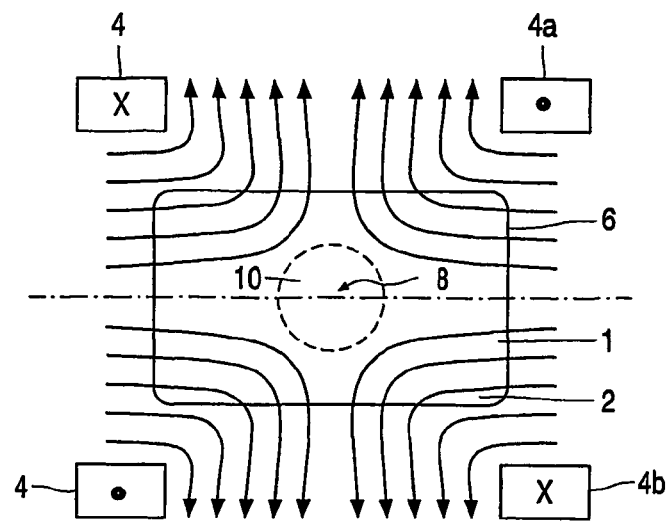
FIG. 1 shows a field line profile of a gradient field used in the method according to the invention.

In order to be able to influence the magnetic particles in the examination object 1 and to generate a gradient field there are a number of pairs of coils above and below the examination object, the range of action of which coils defines the examination area 2. In order also to be able to obtain information about the spatial concentration of the magnetic particles in the examination object 1, further pairs of coils may also be provided (not shown). A first pair of coils 4 in this case comprises the coaxial, identically designed windings 4a and 4b which are arranged above and below the examination object and are flowed through by currents that are of the same strength but have opposite directions. The gradient magnetic field generated thereby is shown in FIG. 1 with the aid of the field lines 6. In the direction of the (perpendicular) axis of the pair of coils it has a virtually constant gradient, and at a point 8 on this axis it reaches the value 0. Starting from this field-free point, the strength of the magnetic field increases in all three spatial directions as the distance increases. In the region 10 (the first part-area) around the field-free point 8, said region being shown in dashed line, the field strength is so low that the magnetization of magnetic particles located there (not shown) is not saturated whereas it is in a state of saturation outside the region 10.

Figure 2:
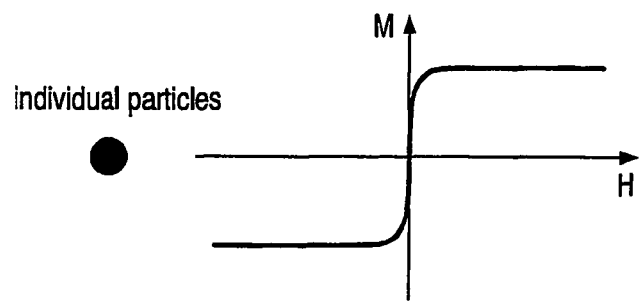
FIG. 2 shows a profile of the magnetization in the presence of free magnetic particles.

FIG. 2 shows the behavior of free, non-coupled and non-agglomerated individual magnetic particles in the weak-field region 10 in the case of a change in the spatial position of said region or in the case of a change in the field strength in this examination area. It can be seen from the diagram that the magnetization of the magnetic particles changes relatively quickly as a function of the magnetic field strength H upon passing through the zero crossing and reaches the saturation state at an appropriately low magnetic field strength. When the magnetic field strength is reversed with a new zero crossing, an identical characteristic is also obtained, i.e. no hysteresis is observed. The magnetic behavior of the magnetic particles can be readily detected in an accurate manner for example by means of suitable coil arrangements.

Figure 3:
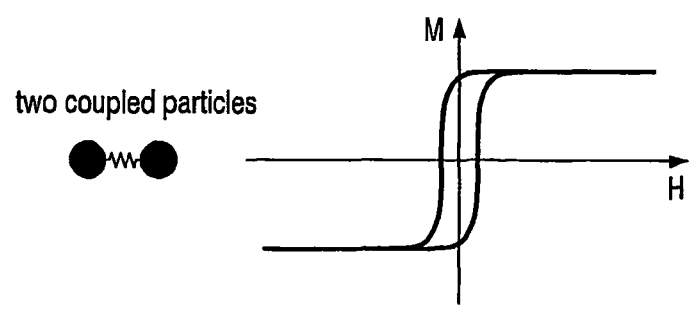
FIG. 3 shows a profile of the magnetization in the case of a field variation parallel to the binding direction.
Figure 4:
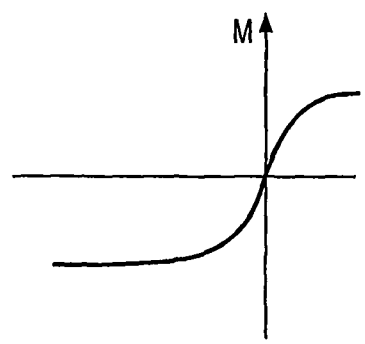
FIG. 4 shows the profile of the magnetization in the case of a field variation perpendicular to the binding direction.

By contrast, the magnetization of coupled magnetic particles, e.g. those which are bound to one another via a covalent spacer unit, exhibits a significantly different magnetization profile than that of free magnetic particles in the weak-field region 10 both in the binding direction and perpendicular to the binding direction. As can be seen in FIG. 3, the magnetization of coupled magnetic particles changes as a function of the magnetic field strength in the binding direction such that hysteresis occurs. If the magnetic behavior of coupled magnetic particles is observed in the case of a change in the magnetic field strength perpendicular to the binding direction, a less steep profile of the magnetic characteristic in the region of the zero crossing is seen compared to that in the case of free magnetic particles (cf. FIG. 4). Accordingly, in this case the saturation magnetization is only achieved at a relatively high field strength. The different magnetic behavior of coupled or agglomerated magnetic particles can then be used to ascertain under which external conditions or influencing variables there is a change to individual free particles. If, for example, it is known under which conditions, e.g. at which temperature or at which pH, a covalent bond is cleaved, then the change in the magnetization behavior in the examination area allows conclusions to be directly drawn about the conditions prevailing there. Of course, the inverse procedure, i.e. the transition of free magnetic particles to coupled or agglomerated particles, and also the extent of the transition, can be ascertained in the same manner.

Figure 5:
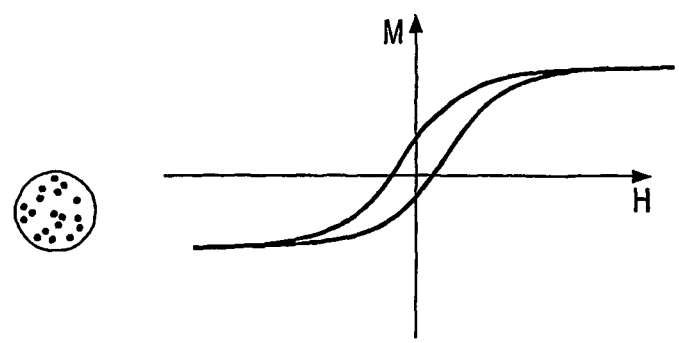
FIG. 5 shows the profile of the magnetization in the case of a particle agglomerate within a shell.

FIG. 5 shows the magnetic behavior of magnetic particles agglomerated in a shell in the weak-field region 10 in the case of a change in the magnetic field strength. In this case, too, a hysteresis behavior is observed in the case of a change in the magnetic field strength with zero crossing, with the saturation magnetization in each case being achieved at a relatively high magnetic field strength compared to that of free magnetic particles. Thus, in the case of magnetic particles that are agglomerated in shells or in droplets both the delayed reaching of the saturation magnetization and also the hysteresis behavior provide information about the state which the magnetic particles in the examination area are in. If, for example, it is known under which conditions a shell material, e.g. of a viscous nature, dissolves, then in this way it is possible to obtain information about the conditions prevailing in the examination area.

The features of the invention that are disclosed in the above description, the drawings and the claims may be essential for the implementation of the invention in its various embodiments both individually and in any desired combination.

The invention claimed is:

1. A method of determining physical, chemical and/or biological state variables in an examination area of an examination object by determining a change in a spatial distribution of magnetic particles in the examination area, the method comprising the acts of:
   introducing into the examination area magnetic particles in a first state or in a second state wherein, in the first state, at least some of the magnetic particles that are to be examined are agglomerated and/or coupled to one another and wherein, in the second state, the particles are deagglomerated and/or decoupled;
   generating a magnetic field having a strength with a spatial profile such that there is produced in the examination area two part-areas including a first part-area having a low magnetic field strength and a second part-area having a higher magnetic field strength than the low magnetic field strength;
   changing spatial positions of the two part-areas in the examination area or changing the magnetic field strength in the first part-area to cause the change in the spatial distribution of magnetic particles so that magnetization of the particles is locally changed;
   detecting signals that depend on the magnetization in the examination area that is influenced by the changing act;
   evaluating the signals so as to obtain information about the change in the spatial distribution of the magnetic particles and about physical, chemical and/or biological state variables, wherein the physical, chemical and/or biological state variables include at least one of substance temperature, pressure, viscosity and pH;
   correlating the change in the spatial distribution of the magnetic particles in the examination area with at least one of a local temperature, pressure, viscosity and pH value to determine the at least one of the local substance temperature, pressure, viscosity and pH;
   determining the at least one of the local substance temperature, pressure, viscosity and pH; and
   providing an indication of the determined at least one of the local substance temperature, pressure, viscosity and pH.

2. The method as claimed in claim 1, wherein the detecting act includes detecting change of the magnetic particles from the first state to the second state including deagglomeration and/or decoupling of coupled individual magnetic particles and/or detecting increased distance between individual magnetic particles.

3. The method as claimed in claim 1, wherein the detecting act includes detecting passage of the magnetic particles between the first state and the second state, the passage being due to at least one of heat, radiation, acid, base, electrical or magnetic fields, ultrasound and/an enzyme.

4. The method as claimed in claim 1, further comprising the act of spatially delimiting the agglomerated magnetic particles in a medium which can be physically, chemically and/or biologically modified, dissolved and/or degraded.

5. The method as claimed in claim 4, wherein the medium comprises polysaccharides, starch, in particular dextrins or cyclodextrins, waxes, oils, fats or gels.

6. The method as claimed in claim 4, the medium comprises microorganisms.

7. The method as claimed in claim 1, further comprising the act of providing the agglomerated magnetic particles on a surface of a particulate.

8. The method as claimed in claim 1, further comprising the act saturating the magnetic particles by application of an external magnetic field having a strength of about 100 mT or less.

9. The method as claimed in claim 1, wherein the magnetic particles comprise multidomain or monodomain particles, and further comprising the act of reversing the magnetization of the multidomain or monodomain particles by Neel's rotation and/Brown's rotation.

10. The method as claimed in claim 1, wherein the magnetic particles are hard-magnetic or soft-magnetic multidomain particles.

11. The method as claimed in claim 1, wherein the magnetic particles are monodomain particles, or soft-magnetic multidomain particles of asymmetric shape, the method further comprising the act of reversing the magnetization of the monodomain particles by Neel's and Brown's rotation.

12. The method as claimed in claim 1, further comprising the acts of:
   binding the magnetic particles to functional binding units including at least one of a functional group, a DNA sequence, an RNA sequence, and an aptamer, and; and
   introducing into the examination area at least one compound which has complementary functional binding units including at least one of a complementary functional group, a complementary DNA sequence, a complementary RNA sequence, and a complementary aptamer sequence, that interacts in a binding manner with at least one functional binding unit of the magnetic particles.

13. The method as claimed in claim 1, wherein evaluating act further comprises the acts of:
   selecting of a path for the movement of the first part-area having a low magnetic field strength within the examination area,
   recording of reference data by using reference samples along the path at at least one location, and in the case of at least two locations, recording external parameters using at least a first receiving coil,
   at least one of interpolating and extrapolating the recorded reference data recorded in respect of points and external parameters not recorded,
   measuring the path within the examination area in a sequence that is substantially identical to that used for the recording of data by the reference samples via a coil arrangement including at least one of the first receiving coil and a second receiving coil, and
   comparing the measured data with the reference data by an error square minimization to obtain compared data.

14. The method as claimed in claim 13, further comprising the act of converting the reference data to characteristics of at least a second receiving coil used for the measuring act.

15. The method as claimed in claim 13, further comprising the act of assigning the compared data obtained by the comparing act to a gray value for a pixel to give an image, with the relative pixel intensity representing a degree of the external parameters determined by at least one of the recording act and the at least one of interpolating and extrapolating acts.

16. The method as claimed in claim 15, wherein the providing act includes the act of displaying the image in a merged image.

17. The method as claimed in claim 13, further comprising one of the acts of:

moving the first part-area having the low magnetic field strength by actuating and/or moving the coil arrangement;

keeping stationary the first part-area having the low magnetic field strength while moving the examination object; and moving simultaneously both the examination object and the first part-area relative to one another.

18. The method of claim 1, wherein the act of changing the magnetic field strength changes the magnetic field strength temporally in a first frequency band, and the detecting act includes detecting the signal in a second frequency band, the second frequency band including harmonics of signals in the first frequency band.

19. The method of claim 1, wherein the act of generating the magnetic field includes the act of first and second magnetic fields which change at different rates and with different amplitudes, wherein the first magnetic field changes slowly in time and with a higher amplitude relative the second magnetic field, and the second magnetic field changes rapidly in time terms and with a lower amplitude relative the first magnetic field.

20. The method of claim 1, wherein the detecting act includes detecting changes in magnetic properties of the magnetic particles due to changed distances between the magnetic particles; the method further comprising the act of producing a contrast in an image of the spatial distribution of the magnetic particles in the examination area based on the detected changes in the magnetic properties.

* * * * *